United States Patent [19]

Pinkos et al.

[11] Patent Number: 5,391,734
[45] Date of Patent: Feb. 21, 1995

[54] PREPARATION OF N-(2-HYDROXYPROPYL)-2,6-DIMETHYL-MORPHOLINE

[75] Inventors: Rolf Pinkos, Bad Durkheim; Hans R. Merkle, Ludwigshafen; Rolf Fischer, Heidelberg, all of Germany

[73] Assignee: BASF Aktiengesellschaft, Ludwigshafen, Germany

[21] Appl. No.: 22,342

[22] Filed: Feb. 25, 1993

[30] Foreign Application Priority Data

Feb. 28, 1992 [DE] Germany .................. 4206171

[51] Int. Cl.6 .................................... C07D 265/30
[52] U.S. Cl. ................................................. 544/170
[58] Field of Search ........................................ 544/170

[56] References Cited

U.S. PATENT DOCUMENTS 4,117,227  9/1978  Brennan ........................ 544/170

FOREIGN PATENT DOCUMENTS 287192  2/1991  German Dem. Rep. .

Primary Examiner—Robert W. Ramsuer
Attorney, Agent, or Firm—Keil & Weinkauf

[57] ABSTRACT

A process for the preparation of N-(2-hydroxypropyl)-2,6-dimethylmorpholine, wherein tris-(2-hydroxypropyl)amine is cyclized
 a) in the presence of acid catalysts or
 b) in the presence of hydrogenation catalysts.

5 Claims, No Drawings

PREPARATION OF N-(2-HYDROXYPROPYL)-2,6-DIMETHYLMORPHOLINE

This invention relates to a process for the preparation of N-(2-hydroxypropyl)-2,6-dimethylmorpholine from tris-(2-hydroxypropyl)amine in the presence of heterogenous catalysts.

DD-A 287,192 discloses that tris-(2-hydroxypropyl)amine cyclizes on treatment with 70% strength sulfuric acid to form N-(2-hydroxypropyl)-2,6-dimethylmorpholine with the elimination of water. The product occurs in protonated form and must be liberated by treatment with caustic soda solution. Aqueous sodium sulfate solution is formed, which must be disposed of by expensive means. Example 1a shows that more than 4 kg of sodium sulfate are formed per kg of N-(2-hydroxypropyl)-2,6-dimethylmorpholine.

It is thus an object of the present invention to overcome the aforementioned disadvantages.

Accordingly, we have found a novel and improved process for the preparation of N-(2-hydroxypropyl)-2,6-dimethylmorpholine, wherein tris-(2-hydroxypropyl)amine is cyclized a) in the presence of acid catalysts or
b) in the presence of hydrogenation catalysts and hydrogen.

The process of the invention may be carried out as follows:

a) The cyclization can be carried out by contacting tris-(2-hydroxypropyl)amine with acid catalysts at a temperature ranging from 100° to 400° C., preferably from 150° to 350° C. and more preferably from 180° to 290° C. and pressures ranging from 0.001 to 50 bar, preferably from 0.01 to 2 bar and more preferably from 0.1 to 1 bar.

The acid cyclization can be carried out continuously or batchwise, and it is preferred to conduct the process in fluid bed or fixed bed reactors, cyclization being effected in the liquid phase or, preferably, in the gas phase.

Another preference is that cyclization be carried out in a vessel containing the catalyst in the liquid phase, the desired product being distilled off. The tris-( 2-hydroxypropyl)amine can be added continuously or batchwise.

The residence time can be, e.g., from 1 to 5 s in the reactions in the gas phase, or from 5 min to 2 h in reactions carried out in the liquid phase.

Examples of suitable acid catalysts are oxides of Group IIIb or Group IVb elements or of Group IIa to Group VIa elements in the periodic table or combinations thereof, such as acidic or superacidic metal oxides of b-group elements e.g., $TiO_2$, $ZrO_2$, $Fe_2O_3$ and ZnO or, e.g., MgO, $B_2O_3$, $Al_2O_3$, $SiO_2$, and $SnO_2$ or combinations thereof, such as $TiO_2/ZnO$ or $Al_2O_3/MgO$. To increase the acid strength, the oxides can be treated with acids such as sulfuric acid or phosphoric acid.

Other examples of suitable acid catalysts are zeolites, e.g., representatives of the mordenite species or fine-pored zeolites of the erionite or chabasite species or zeolites of the faujasite species, e.g., type Y, type X or type L zeolites and the "ultrastable" faujasite-type zeolites, i.e., dealuminated zeolites.

Zeolites having a pentasil structure are also suitable, such as ZSM-5, ZSM-11 and ZBM-10. These have in common a foundation block comprising a five-membered ring composed of $SiO_2$ tetrahedra. They are characterized by a high $SiO_2/Al_2O_3$ ratio and by pore sizes lying between those of the type A zeolites and those of type X or type Y zeolites.

Equally suitable are stratified silicates such as, e.g., Tonsil, which can be doped with aluminum, or alumosilicates.

Furthermore, heteropoly acids are suitable. These are inorganic poly acids which possess, unlike isopoly acids, at least two different center atoms. Examples thereof are dodecatungstophosphoric acid $H_3PW_{12}O_{40}.H_2O$, and dodecamolybdophosphoric acid $H_3PMO_{12}O_{40}.H_2O$. In principle, the catalysts mentioned in EP-A 158,229 can be used as well as combinations of catalysts.

Preferred heteropoly acids are heteropoly acids of molybdenum or tungsten with phosphoric acid, telluric acid, selenic acid, arsenic acid, silicic acid, especially phosphoric acid.

The protons of the heteropoly acids can be partially replaced by metal ions, of which alkali metal and alkaline-earth metal ions are preferred.

Also suitable are phosphates, hydrogen phosphates and polyphosphates, which can contain alkali metal or alkaline-earth metal ions.

In principle, combinations of the catalysts stated are suitable, e.g., combinations of aluminum oxides which have been modified by acids such as sulfuric or phosphoric acid, and heteropoly acids.

b) The cyclization of tris-(2-hydroxypropyl)amine can be carried out in contact with hydrogenation catalysts at a temperature ranging from 150° to 350° C., preferably from 180° to 310° C. and at pressures ranging from 1 to 300 bar, preferably from 3 to 100 bar and more preferably from 4 to 50 bar in the gas phase or, preferably, in the liquid phase. The reaction can be effected without the addition of hydrogen, but it is preferred to operate in the presence of hydrogen. The reaction pressure is essentially determined by the hydrogen pressure applied during pressurization and by the pressure change occurring when heat is applied in sealed high-pressure equipment.

The process can be carried out batchwise, e.g., in autoclaves, or preferably continuously, e.g., in tubular reactors.

Examples of suitable catalysts are all catalysts which have a hydrogenating action, for example those which are capable of hydrogenating ketones or aldehydes catalytically to alcohols by means of hydrogen.

Examples thereof are described in Houben-Weyl, *Methoden der organischen Chemie*, Vol. IV/1c, Georg Thieme Verlag, Stuttgart, 1980, pp. 16–28, 68, 189–224. Suitable hydrogenation catalysts are, e.g., Group Ib elements and Group VIb–VIIIb elements in the periodic table, e.g., in the form of the metals, their oxides or their sulfides. They can be used, e.g., as supported catalysts, skeleton catalysts, black catalysts, or mixed metal catalysts. Examples are platinum black, Pt/C, $Pt/Al_2O_3$, $PtO_2$, palladium black, Pd/C, $Pd/Al_2O_3$, $Pd/SiO_2$, $Pd/CaCO_3$, $Pd/BaSO_4$, Rh/C, $Rh/Al_2O_3$, $Ru/SiO_2$, $Ni/SiO_2$, Raney nickel, $Co/SiO_2$, $Co/Al_2O_3$, Raney cobalt, Fe, iron-containing catalyst mixtures, rhenium black, Raney rhenium, $Cu/SiO_2$, $Cu/Al_2O_3$, Raney copper, Cu/C, $PtO_2/Rh_2O_3$, Pt/Pd/C, $CuCr_2O_4$, $BaCr_2O_4$, $Ni/Cr_2O_3/Al_2O_3$, $Re_2O_7$, CoS, NiS, $MoS_3$, $Cu/SiO_2/MoO_3/Al_2O_3$ or combinations thereof.

Preferred catalysts are those containing copper as active component, e.g., in concentrations of from 2 to 90 wt %, preferably from 10 to 80 wt %,.

The catalysts need not necessarily be activated prior to the reaction.

The residence time usually ranges from 5 min to 3 h.

In the variants a) and b), isomer mixtures comprising cis- and trans-N-(2-hydroxypropyl)-2,6-dimethylmorpholines are formed in a ratio of ca 3:1.

It is surprising that the remaining hydroxyl group of the N-(2-hydroxypropyl)-2,6-dimethylmorpholine remains largely intact under the conditions of the invention, since Houben-Weyl, Vol. V/1b, Georg Thieme Verlag, Stuttgart, 1972, pp. 45 to 83, discloses that secondary hydroxyl groups form olefin and water at temperatures exceeding 200° C. in the presence of the catalysts of the invention.

N-(2-hydroxypropyl)-2,6-dimethylmorpholine can be used, e.g., as starting material for fungicides for combating phytopathogenic fungi (DD-A 287,195).

EXAMPLES

EXAMPLE 1

In a fluid bed furnace (capacity 300 mL) tris-(2-hydroxypropyl)amine (20 g/h, purity 90%) was evaporated (1013 mbar) in a hot nitrogen stream (60 L/h) and reacted at 220° C. over a catalyst mixture of 80 g of an aluminum oxide doped with phosphoric acid (5 wt %) and 40 g of dried molybdatophosphoric acid for a period of 8 h. The dark-colored effluent consisted of two phases. The bottom phase mainly comprised water of reaction, whilst the organic top phase contained, as determined by gas-chromatographic analysis, 77 wt % of N-(2-hydroxypropyl)-2,6-dimethylmorpholine in addition to 3 wt % of educt.

EXAMPLE 2

In a repetition of Example 1 but using 100 g of an aluminum oxide doped with phosphoric acid (5 wt %) as catalyst (particle size from 0.1 to 0.3 mm), there were obtained, at 220° C. and a reaction time of 6 h, 62 wt % of N-(2-hydroxypropyl)-2,6-dimethylmorpholine in addition to 21 wt % of educt.

N-(2-hydroxypropyl)-2,6-dimethylmorpholine could be readily separated, by distillation, from unconverted tris-(2-hydroxypropyl)amine, which can be recycled to the reaction.

EXAMPLE 3

In a reaction vessel equipped with drip funnel and distillation head there were placed 2.5 g of aluminum oxide doped with phosphoric acid (5%) and heated to 290° C. tris-(2-Hydroxypropyl)amine, preheated to 60° C., was continuously fed dropwise to the reaction vessel via the drip funnel, under a slow stream of gas (nitrogen). Volatile products were distilled off via the distillation head and condensed, and the condensate formed two phases. The bottom phase consisted predominantly of water. 12 g of tris-(2-hydroxypropyl)amine were added dropwise over a period of one hour. The effluent was analyzed following periods of 5 min, 30 min, and 60 min. The organic phase then contained 26 wt % (1.5 g), 63 wt % (3.6 g), and 65 wt % (3.7 g), respectively, of N-(2-hydroxypropyl)-2,6-dimethylmorpholine and 3 wt %, 3 wt %, and 5 wt %, respectively, of educt. The total yield of N-(2-hydroxypropyl)-2,6-dimethylmorpholine in the distillate was 52 mol %. In the reaction vessel there remained ca 2 g of organic phase, in which 15 wt % of N-(2-hydroxypropyl)-2,6-dimethylmorpholine and 37 wt % of educt were present.

EXAMPLE 4

3 g of tris-(2-hydroxypropyl)amine and 1 g of Tonsil were heated for 45 min at 290° C. in a glass vessel having a capacity of 50 mL. On cooling, and removal of the catalyst by filtration, GC analysis indicated 35 wt % of N-(2-hydroxypropyl)-2,6-dimethylmorpholine in addition to 12 wt % of educt.

EXAMPLE 5

3 g of tris-(2-hydroxypropyl)amine and 1 g of $SnO_2$ doped with sulfuric acid were heated in a manner similar to that described in Example 3 for a period of 1 h at 250° C. There were obtained, in addition to 50 wt % of educt, 30 wt % of N-(2-hydroxypropyl)-2,6-dimethylmorpholine.

EXAMPLE 6

In a metallic autoclave having a capacity of 50 mL there were placed 10 g (90 wt % strength) of tris-(2-hydroxypropyl)amine and 2.7 g of a catalyst activated with hydrogen (56 wt % of CuO, 44 wt % $Al_2O_3$), and it was pressurized with 5 bar of hydrogen and heated for 1 h at 250° C. The pressure rose during the heating period to 35 bar. On cooling, and depressurization, the catalyst was removed by filtration and the two-phase filtrate (10 g) was homogenized with ethanol and analyzed by gas-chromatographic techniques. In addition to 3 wt % of educt 67 wt % of N-(2-hydroxypropyl)-2,6-dimethylmorpholine (ratio of cis/trans isomers ca 3:1) was present.

EXAMPLE 7

In a manner similar to that described in Example 6, a Cu catalyst was used (10 wt % of CuO, 90 wt % of C, activated). On achieving quantitative conversion 87 wt % of N-(2-hydroxypropyl)-2,6-dimethylmorpholine was present in the effluent.

EXAMPLE 8

In a manner similar to that described in Example 6, use was made of a catalyst containing predominantly copper (37 wt % of CuO, 29 wt % of $SiO_2$, 14 wt % of MgO, remainder BaO, $Cr_2O_3$, ZnO and water, activated). In addition to 3 wt % of educt the effluent contained 77 wt % of N-(2-hydroxypropyl)-2,6-dimethylmorpholine.

EXAMPLE 9

In a manner similar to that described in Example 6, a Pd/Re catalyst was used (3 wt % of Be, 3 wt % of Pd on activated charcoal). In addition to 3 wt % of educt the effluent contained 60 wt % of N-(2-hydroxypropyl)-2,6-dimethylmorpholine.

EXAMPLE 10

In a metallic autoclave having a capacity of 2500 mL there were placed 900 g (90 wt % strength) Of tris-(2-hydroxypropyl)amine and 160 g of a cu catalyst (10 wt % of CuO, 90 wt % of C, activated). The autoclave was pressurized with 5 bar of $H_2$ and heated for 2 h at 250° C. The reaction pressure rose to 35 bar. On cooling, the catalyst was filtered off and the filtrate distilled. In addition to 105 g of educt 500 g of pure N-(3-hydroxypropyl)-2,6-dimethylmorpholine could be isolated.

We claim:

1. A process for the preparation of N-(2-hydroxypropyl)-2,6-dimethylmorpholine, wherein tris-(2-hydroxypropyl)amine is cyclized.

2. A process as defined in claim 1 for the preparation of N-(2-hydroxypropyl)-2,6-dimethylmorpholine, wherein the hydrogenation catalysts used are Group Ib elements or Group VIb–VIIIb elements in the periodic table.

3. A process as defined in claim 1 for the preparation of N-(2-hydroxypropyl)-2,6-dimethylmorpholine, wherein the hydrogenation catalysts used are Group Ib elements or Group VIb–VIIIb elements in the periodic table in the form of their metals, their oxides, or their sulfides.

4. A process as defined in claim 1 for the preparation of N-(2-hydroxypropyl)-2,6-dimethylmorpholine, wherein the hydrogenation catalysts contain copper.

5. A process as defined in claim 1 for the preparation of N-(2-hydroxypropyl)-2,6-dimethylmorpholine, wherein the reaction is carried out in the presence of hydrogenation catalysts at a temperature ranging from 150° to 350° C.

* * * * *